United States Patent [19]
Hanes et al.

[11] Patent Number: 4,658,069
[45] Date of Patent: Apr. 14, 1987

[54] CONVERSION OF ALLYL ETHERS TO ACETALS

[75] Inventors: Ronnie M. Hanes, Milford; William D. Baugh, Wilmington, both of Ohio

[73] Assignee: National Distillers and Chemical Corporation, New York, N.Y.

[21] Appl. No.: 751,094

[22] Filed: Jul. 2, 1985

[51] Int. Cl.$^4$ ............................................. C07C 43/303
[52] U.S. Cl. ..................................... 568/603; 568/605; 568/594; 560/186; 260/410.6; 260/410.9 R
[58] Field of Search ....................... 568/594, 603, 605; 560/186; 260/410.6, 410.9 R

[56] References Cited

U.S. PATENT DOCUMENTS 3,584,010 6/1971 Morbet ................................. 568/594

FOREIGN PATENT DOCUMENTS 53-37325 10/1978 Japan.
53-37326 10/1978 Japan.

OTHER PUBLICATIONS

Moisiev et al. I, Acad. Sci. USSR, Dokl. Chem. Section, 1960, pp. 804–804.
Moisiev et al. II, Soviet Inventions Illustrated, Mar. 1965.
Stern et al., Proceedings Chem. Soc., Oct. 1961, p. 370.

Primary Examiner—Howard T. Mars
Attorney, Agent, or Firm—Kenneth D. Tremain

[57] ABSTRACT 9-methoxy-7-nonenal may be isomerized in the presence of methanol and ruthenium chloride to provide 1,1,9,9-tetramethoxynonane. The rates of reaction are increased by pre-formation of 1,1,9-trimethoxy-7-nonene and removal of the water generated prior to conducting the isomerization reaction.

19 Claims, No Drawings

CONVERSION OF ALLYL ETHERS TO ACETALS

DESCRIPTION

1. Technical Field

The invention is directed to the conversion of an allylic ether to an acetal in the presence of an isomerization catalyst.

2. Prior Art

Yamahara et al., Japanese Pat. No. 53-37325 discloses the formation of an acetal by the reaction of 1-methoxy-2,7-octadiene with methanol in the presence of ruthenium chloride under a nitrogen blanket, anhydrous conditions and at a temperature of 50° C. for two hours in an autoclave lined with titanium.

SUMMARY OF THE INVENTION

The present invention relates to a method for converting the ether group of an allylic ether to an acetal group by reacting an organic hydroxy compound with an allylic ether containing a formyl or carboxy substituent. The reaction is conducted in two stages. In the first stage the formyl or carboxy group is converted to an acetal or ester group and water. The water is removed and the second stage reaction is carried out to convert the ether to an acetal under anhydrous conditions in the presence of a catalytically effective amount of a catalyst comprising a metal compound where the metal is selected from Group VIII of The Periodic Table of the Elements and mixtures of such metal compounds. The organic hydroxy compound is reacted with the ether so that an acetal is formed due in part to the isomerization of the allyl moiety to a vinyl moiety. By employing anhydrous conditions the isomerization reaction proceeds at faster rates and lower temperatures.

DETAILED DESCRIPTION OF THE INVENTION

The invention relates to a method for the conversion of an allylic ether to an acetal and especially the conversion of an allylic ether having a formyl or carboxy substituent to an acetal.

The allylic ethers are those compounds having the formula:

     I where $R^1$ comprises an organo group, especially a cyclic or acyclic hydrocarbon group having from 1 to about 12 and especially from 1 to about 8 carbon atoms and substituted with a formyl group or carboxy group. $R^1$ especially may comprise an alkyl, alkenyl, aryl or alkaryl group or an alkyl, alkenyl, aryl or alkaryl group having an ester, ether, or ketone substituent in addition to a formyl or carboxy group. The radical $R^2$ also comprises said organo group, especially a cyclic or acyclic hydrocarbon group having from 1 to about 12 and especially from 1 to about 8 carbon atoms such as an alkyl or aralkyl group. $R^2$ in one embodiment comprises said organo group that is not substituted with a formyl group or carboxy group. With respect to both the $R^1$ and $R^2$ groups where said groups comprise alkyl groups, the various structural isomers of these alkyl groups are also intended to be included in the foregoing definition.

One class of allylic ethers that are preferably reacted to form an acetal according to the present invention may be described as 1-alkoxy-2-alkenal compounds especially those compounds where the alkoxy group is a lower alkoxy having from 1 to about 6 carbon atoms preferably 1 to about 4 carbon atoms and the various structural isomers thereof. That portion of the above-identified molecule defined as "2-alkenal" is an aldehyde moiety having from about 4 to about 20 carbon atoms, especially from about 4 to about 15 carbon atoms and preferably from about 6 to about 12 carbon atoms.

Although the identification of aldehydes according to IUPAC terminology requires that the numbering of the carbon atoms in the molecule be such that the aldehyde group is designated as containing the first carbon atom, the above terminology has been chosen in order to generically describe the various classes of unsaturated aldehydes having allylic unsaturation employed according to the invention and has been chosen as a matter of convenience in broadly describing the compounds.

Examples of compounds that fall within the broad class of compounds designated by Formula I above as well as those described herein as 1-alkoxy-2-alkenal compounds include: 5-methoxy-3-pentenal, 6-methoxy-4-hexenal, 7-methoxy-5-heptenal, 8-methoxy-6-octenal, 9-methoxy-7-nonenal, 10-methoxy-8-decenal, 8-ethoxy-6-octenoic acid, 7-ethoxy-5-heptenoic acid, 5-ethoxy-3-pentenoic acid, 5-allyloxypentenal, and the like.

In one embodiment of the present invention it has been discovered that the conversion proceeds by reacting the aforesaid ethers with an organic hydroxy compound in the presence of a catalyst. This catalyst is sometimes referred to as an isomerization catalyst and is based on a metal selected from Group VIII of The Periodic Table of the Elements, especially the Group VIII noble metals comprising ruthenium, rhodium, palladium, osmium, iridium and platinum and preferably, ruthenium, rhodium, palladium and platinum. The most preferred metal in this respect comprises ruthenium. The halides of such metals comprise a preferred catalyst, such as the chlorides, bromides and iodides, the chlorides being especially preferred.

Other catalysts that may be used according to the invention include: iridium chloride, iridium bromide, rhodium chloride, rhodium bromide, ruthenium bromide, ruthenium iodide, and the like.

The organic hydroxy compound comprises any saturated or unsaturated organic compound having at least one hydroxy group and is either a straight chain, branched chain, cyclic or heterocyclic compound and has from 1 to about 10 carbon atoms and preferably comprises alkanols having from 1 to about 10 carbon atoms and preferably lower alkanols having from 1 to about 6 carbon atoms and most preferably 1 to about 4 carbon atoms. The structural isomers of the foregoing alkanols may also be employed. Additionally, various mixtures of any of the foregoing organic hydroxy compounds may also be employed according to one embodiment of the present invention. The organic hydroxy compound generally comprises any compound that will etherify with the vinyl unsaturation such as the alkanols and especially the lower alkanols.

Other hydroxy compounds that may be used according to the invention include: glycols such as 1,2-ethylene glycol, 1,2-propylene glycol, 1,3-propylene glycol; 1,2-butanediol, 1,3-butanediol, and the like.

It is essential to the present invention that the conversion process be carried out under anhydrous conditions and that any water formed as a by-product of the reaction be removed.

One of the features of the present invention is the discovery that the reaction promoted by the catalyst described herein proceeds at a faster rate and at lower temperatures under anhydrous conditions than when water is present. It is therefore essential that water formed during the first stage of the reaction, be removed after which the reactants are contacted with the catalyst in a second stage and the ether is converted to an acetal under anhydrous conditions.

Water removal may be effected by conventional means which are known in the art such as by using a molecular sieve that combines with water, by distillation at atmospheric pressure, superatmospheric pressure or in vacuuo or by extracting the organic components from the water that is formed by means of a solvent that is water immiscible such as hexane and the like.

In this respect the molecular sieves and solvents that may be suitably employed according to the invention are easily determined by a skilled artisan and include: molecular sieve 3A, 4A and 13A. Whereas the solvents include: water-immiscible solvents such as pentane, hexane, toluene, xylene, methylene chloride, chloroform, and the like.

The temperature and pressure conditions as well as the time for conducting such water extraction methods are conventional and are well within the knowledge of an organic chemist having ordinary skill in the art.

Since the overall reaction results in the production of water it is conducted in two stages in which water is removed in the first stage and the isomerization catalyst is not employed until the second stage wherein the water-free product of the first stage is isomerized and converted to an acetal.

By way of example, the two-stage reaction is employed where the ether having allylic unsaturation also contains an aldehyde group. Since the isomerization of the allylic unsaturation to vinyl unsaturation may be conducted in the presence of an organic hydroxy compound as well as the isomerization catalyst, this organic hydroxy compound and especially the lower alkanols also will react with the aldehyde to form an acetal and water. Accordingly, this aspect of the reaction is conducted as a separate process in a first stage without the isomerization catalyst whereby the aldehyde is converted into an acetal and water and the water removed as noted above, i.e., by means of a molecular sieve or by separating the organic components of the reaction from the water phase formed by means of water immiscible solvents such as hexane and the like. The water-free allylic acetal ether obtained is then isomerized by means of the catalyst in the second stage and reacted with additional organic hydroxy compound to form the diacetal. The same procedure is used where the allylic ether contains a carboxy substituent that is converted to an ester.

It has also been found that the formation of the acetal in the first stage proceeds more rapidly in the presence of an acid catalyst such as an acidic ion exchange resin e.g. Dowex-50 (trademark). Other catalyst may be employed and comprise Amberlite IR-120 (trademark) or Amberlite 252 (trademark).

After the first stage reaction is completed and the water removed, an allylic ether such as an allylic acetal ether or allylic ester ether is obtained and is subsequently contacted with the catalyst comprising the Group VIII metal compound in a second stage reaction.

An organic hydroxy compound is employed in the second stage, the organic hydroxy compound being either different from or the same as that employed in the first stage reaction.

In the second stage of the two-stage reaction, the water-free reactant comprising an acetal ether or ester containing allylic unsaturation is combined with the catalyst and an organic hydroxy compound and the allylic unsaturation is isomerized to vinyl unsaturation. An organic hydroxy compound such as an alkanol as previously defined herein is employed as one of the reactants and during the isomerization reaction, combines with the vinyl unsaturation produced to form the corresponding diacetal or acetal ester.

The starting material for the second stage of the reaction is therefore a compound of the formula:

   II wherein at least one of $R^3$ or $R^1$ or $R^3$ or $R^2$ contains an ester group or acetal group. $R^3$ is based on the organic hydroxy compound defined herein and is otherwise the same as previously defined. $R^2$ is the same as previously defined. The substituent $R^3$ is therefore hydrogen or any organic saturated or unsaturated acetal or carboxylate moiety and is either straight chain, branched chain, cyclic or heterocyclic and has from 1 to about 10 carbon atoms such as straight chain or branched chain having from 1 to about 10 carbon atoms and especially from 1 to about 6 carbon atoms and most preferably 1 to about 4 carbon atoms.

In the two-stage reaction, the first stage is conducted at room temperature and atmospheric pressures and the second stage at about 120° to about 200° C., and especially about 140° to about 170° C. at autogenous pressure or that pressure that will keep the organic hydroxy compound from boiling off, e.g., about 200 to about 400 psig where alkanols are used such as methanol.

By way of example, it has been found that when reacting 9-methoxy-7-nonenal with methanol in the presence of ruthenium chloride that 1,1,9,9-tetramethoxynonane (the diacetal) is produced and the reaction takes place at about 160° C. and requires approximately 180 minutes to get appreciable conversions (20 percent). When the reaction is conducted in two stages whereby in the first stage methanol is reacted with 9-methoxy-7-nonenal in the presence of an acidic ion exchange resin to obtain the mono-acetal 1,1,9-trimethoxy-7-nonene and one mole of water and the water separated prior to isomerization the subsequent isomerization of the monoacetal in the presence of ruthenium chloride and methanol to produce the diacetal in a second stage proceeds at about 160° C. for about 20 minutes to obtain similar conversions.

The following examples are illustrative.

EXAMPLE 1

5 ml. of 9-methoxy-7-nonenal and 5 ml. methanol were charged to a 50 ml Pyrex tube containing 0.3 g. of an ion exchange resin Dowex-50 (trademark). The reaction was stirred using a magnetic bar and proceeded at ambient temperature (approximately 20° C.) and ambient pressures. At the end of 120 minutes, the tube was discharged and the product analyzed and found to contain 1,1,9-trimethoxy-7-nonene and water in a 1:1 molar ratio.

EXAMPLE 2

The procedure of Example 1 was followed; however, 1.0 g. of Dowex-50 was employed as the catalyst. Substantially, the same results were obtained as in Example 1.

EXAMPLE 3

The 1,1,9-trimethoxy-7-nonene of Example 1 and Example 2 was separated from the water produced as a by-product of the reaction by passing through a column of Linde Molecular Sieve 3A. Methanol was similarly dried and 5 ml. of each was charged to a 71 ml. Parr bomb along with 0.0137 g. $RuCl_3$ hydrate. The bomb was sealed and placed in shaker oven at 150° C. for a period of 4 hours. The bomb was opened and the product analyzed and was found to contain 3.7 ml of the diacetal 1,1,9,9-tetramethoxynonane.

EXAMPLE 4

As a comparison, 5.0 ml. 9-methoxy-7-nonenal, 5 ml. methanol and 0.0137 g. $RuCl_3$ hydrate (1.4 percent $H_2O$) were charged to a 71 ml. Parr bomb, the bomb sealed and placed in a shaker oven at 150° C. for 4 hours. The products were analyzed and were found to contain only 0.7 ml. of 1,1,9,9-tetramethoxynonane.

By comparison to Examples 2 and 3, it can be seen that by forming the intermediate 1,1,9-trimethoxy-7-nonene and water after which the water is removed, that the isomerization of the allylic ether to the vinyl ether in the presence of $RuCl_3$ and methanol proceeds at a much faster rate. This is due to the removal of the water from the reaction. This is unexpected in view of the fact that the catalyst $RuCl_3$ was employed in its hydrate form. The water of hydration in the catalyst did not interfere with the isomerization reaction whereas the additional water formed in the production of the intermediate 1,1,9-trimethoxy-7-nonene did.

The various acetals formed according to the present invention may be reacted with water to form the aldehyde followed by air oxidation (e.g., bubbling air through the aldehyde) to form the organic acid.

Where the present invention is employed for the manufacture of the diacetal such as 1,1,9,9-tetramethoxynonane, the diacetal similarly is reacted with water to form the dialdehyde which is reduced with hydrogen to form a diol or reacted with ammonia to form a diamine. The diol may be reacted with a polycarboxylic acid to form a polyester. Low molecular weight polyesters may be used as plasticizers or functional fluids, e.g., hydraulic fluids. The diamine may be reacted with a polycarboxylic acid to form a high molecular weight polyamide useful in forming fibers.

Although the invention has been described by reference to some embodiments, it is not intended that the novel method be limited thereby but that modifications thereof are intended to be included as falling within the broad scope and spirit of the foregoing disclosure and the following claims.

What is claimed is:

1. A method for converting the ether group of an allylic ether to an acetal group, said allylic ether having formyl or carboxy groups, comprising contacting said allylic ether under anhydrous conditions with an alkanol in a first stage, removing water formed in said first stage to obtain a product and contacting said product in a second stage with an alkanol and a catalytically effective amount of a catalyst comprising a metal compound where said metal is selected from Group VIII metals of The Periodic Table of the Elements and mixtures thereof.

2. The method of claim 1 where said metal is selected from the Group VIII noble metals and mixtures thereof.

3. The method of claim 2 where said metal is selected from ruthenium, rhodium, palladium and platinum and mixtures thereof.

4. The method of claim 2 where said metal comprises ruthenium.

5. The method of claim 1 where said first stage is conducted at room temperature and pressure and said second stage is conducted at temperatures of from about 100° to about 200° C. and at pressures of from about 100 to about 800 psig.

6. The method of claim 3 where said catalyst comprises a metal halide.

7. The method of claim 6 where said catalyst comprises a metal chloride, bromide or iodide.

8. The method of claim 6 where said ether comprises an allylic ether having a formyl substituent.

9. The method of claim 8 where said allylic ether comprises an alkyl allylic ether.

10. The method of claim 9 where said allylic ether comprises a lower alkyl allylic ether.

11. The method of claim 6 where said ether comprises an allylic ether having a carboxy substituent.

12. The method of claim 2 where said allylic ether comprises a 1-alkoxy-2-alkenal.

13. The method of claim 12 where said alkanol utilized in said first stage and said alkanol used in said second stage are the same.

14. The method of claim 13 where said alkanol is a lower alkanol.

15. The method of claim 14 wherein said allylic ether comprises 9-methoxy-7-nonenal.

16. The method of claim 15 where said lower alkanol comprises methanol.

17. The method of claim 1 where said metal comprises ruthenium.

18. The method of claim 1 where said metal catalyst comprises a Group VIII metal halide.

19. The method of claim 1 where said catalyst comprises ruthenium chloride.

* * * * *